(12) United States Patent
Cronan, Jr. et al.

(10) Patent No.: US 7,008,545 B2
(45) Date of Patent: Mar. 7, 2006

(54) SYNERGISTIC BIOCIDAL MIXTURES

(75) Inventors: John M. Cronan, Jr., Jacksonville, FL (US); Michael J. Mayer, Jacksonville, FL (US)

(73) Assignee: Hercules Incorporated, Wilmington, DE (US)

(*) Notice: Subject to any disclaimer, the term of this patent is extended or adjusted under 35 U.S.C. 154(b) by 0 days.

(21) Appl. No.: 10/266,509

(22) Filed: Oct. 8, 2002

(65) Prior Publication Data

US 2004/0035803 A1 Feb. 26, 2004

Related U.S. Application Data

(60) Provisional application No. 60/405,235, filed on Aug. 22, 2002.

(51) Int. Cl.
*C02F 1/50* (2006.01)

(52) U.S. Cl. .................. 210/755; 162/161; 210/756; 210/759; 210/760; 210/764; 422/36; 422/37; 514/365; 514/372; 514/528; 514/634; 514/635; 514/642; 514/643; 514/669; 514/693

(58) Field of Classification Search ................ 210/755, 210/756, 758, 759, 764, 760; 422/35–37; 162/161; 514/241, 365, 372, 634, 635, 642, 514/643, 693, 528, 669
See application file for complete search history.

(56) References Cited

U.S. PATENT DOCUMENTS

| | | | |
|---|---|---|---|
| 3,970,755 A | 7/1976 | Gazzard et al. ............ 424/270 |
| 3,975,271 A | 8/1976 | Saunier et al. ............ 210/754 |
| 4,137,166 A | 1/1979 | Heimberger et al. ........ 210/756 |
| 4,725,623 A | 2/1988 | Whitekettle et al. ........ 514/634 |
| 4,725,624 A | 2/1988 | Whitekettle et al. ........ 514/643 |
| 4,732,905 A | 3/1988 | Donofrio et al. ........... 514/372 |
| 4,732,913 A | 3/1988 | Donofrio et al. ........... 514/528 |
| 4,745,132 A | 5/1988 | Swered et al. ............. 514/634 |
| 4,857,557 A | 8/1989 | Donofrio et al. ........... 514/711 |
| 4,859,708 A | 8/1989 | Donofrio et al. ........... 514/727 |
| 4,879,306 A | 11/1989 | Henkels et al. ............ 514/441 |
| 4,916,164 A | 4/1990 | Whitekettle et al. ........ 514/665 |
| 4,966,775 A | 10/1990 | Donofrio et al. ........... 424/661 |
| 5,023,267 A | 6/1991 | Clarkson et al. ........... 514/372 |
| 5,039,708 A | 8/1991 | Conlan et al. ............. 514/705 |
| 5,041,463 A | 8/1991 | Whitekettle et al. ........ 514/634 |
| 5,063,214 A | 11/1991 | Whitekettle et al. .......... 514/75 |
| 5,118,713 A | 6/1992 | Donofrio et al. ........... 514/709 |
| 5,134,160 A | 7/1992 | Whitekettle et al. ........ 514/479 |
| 5,416,122 A | 5/1995 | Donofrio et al. ........... 514/709 |
| 5,494,588 A * | 2/1996 | LaZonby ................... 210/755 |
| 5,519,141 A * | 5/1996 | Nita et al. ................. 548/213 |
| 5,763,482 A | 6/1998 | Paterson et al. ............ 514/526 |
| 5,976,386 A | 11/1999 | Barak ....................... 210/756 |
| 6,069,142 A * | 5/2000 | Gaffney et al. ............. 514/241 |
| 6,132,628 A | 10/2000 | Barak ....................... 210/756 |
| 6,322,749 B1 * | 11/2001 | McCarthy et al. ............ 422/37 |
| 6,369,104 B1 | 4/2002 | Kleina et al. .............. 514/528 |
| 6,413,929 B1 | 7/2002 | Wehlage et al. ............ 510/500 |
| 6,478,973 B1 * | 11/2002 | Barak ....................... 210/756 |

FOREIGN PATENT DOCUMENTS

| | | |
|---|---|---|
| EP | 0 185 970 | 7/1986 |
| EP | 0403465 | 12/1990 |
| EP | 0517102 | 12/1992 |
| EP | 0 252 278 | 1/1998 |
| EP | 0 913 091 | 5/1999 |
| EP | 1 001 012 | 5/2000 |
| EP | 1 080 641 | 3/2001 |
| GB | 1600289 | 10/1981 |
| WO | WO 96 14092 | 1/1988 |
| WO | WO 96 39825 | 12/1996 |
| WO | WO 98 41088 | 9/1998 |
| WO | WO 01 53216 | 7/2001 |

* cited by examiner

*Primary Examiner*—Peter A. Hruskoci
(74) *Attorney, Agent, or Firm*—Joanne Rossi

(57) ABSTRACT

Synergistic mixtures of biocides and their use to control the growth of microorganisms in aqueous systems are disclosed. The method of using the synergistic mixtures entails adding an effective amount of a nitrogenous compound activated by an oxidant and at least one non-oxidizing biocide to an aqueous system. The amount of activated nitrogenous compound and non-oxidizing biocide is selected to result in a synergistic biocidal effect.

29 Claims, No Drawings

SYNERGISTIC BIOCIDAL MIXTURES

CROSS REFERENCE TO RELATED APPLICATIONS

This application is related to U.S. Provisional Patent Application Ser. No. 60/405,235, filed Aug. 22, 2002, from which priority is claimed.

FIELD OF THE INVENTION

The present invention relates to synergistic mixtures (or combinations) of biocides and their use to control the growth of microorganisms in aqueous systems, more particularly in industrial process waters, and most particularly in pulp and paper process systems.

BACKGROUND OF THE INVENTION

Uncontrolled growth of microorganisms can have serious consequences such as degradation or spoilage of products, contamination of products, and interference with a wide range of important industrial processes. Growth of microorganisms on surfaces exposed to water (e.g., recirculation systems, heat exchangers, once-through heating and cooling systems, pulp and paper process systems, etc.) can be especially problematic, because biofilms can be formed by the indigenous microbial species. Depending on the environment, biofilms may develop into thick gelatinous-like masses and are referred to as slime. Slime producing microorganisms include bacteria, airborne microorganisms, sulfate reducing bacteria, filamentous bacteria, spore forming bacteria, fungi and algae.

Slime formation becomes especially problematic in industrial settings, because the presence of slime can interfere with a range of processes, systems, and production. As an example, slime deposits deteriorate cooling towers made of wood and promote corrosion when deposited on the metal surfaces of cooling water systems. Furthermore, slime deposits tend to plug or foul pipes, valves and flowmeters and reduce heat exchange or cooling efficiency on heat exchange surfaces.

Paper production is adversely affected by slime formulation. Pulp and paper mill systems operate under conditions which encourage the growth of microorganisms and often result in fouling problems. Moreover, microorganisms can form large slime deposits which can become dislodged from system surfaces and become incorporated into the paper, which results in increased breaks and tears in the sheet. Furthermore, slime can cause unsightly blemishes or holes in the final product, which result in a lower quality product or the product being rejected. This necessitates shutting down the paper making process to clean the equipment, which results in the loss of production time.

Slime may also be objectionable from the standpoint of cleanliness and sanitation in breweries, wineries, dairies and other industrial food and beverage process water systems. Moreover, sulfate reducing bacteria are often problematic in waters used for the secondary recovery of petroleum or for oil drilling in general. Sulfate reducing bacteria can form slime deposits. However, the real problem with sulfate reducing bacteria is that they become incorporated into well-established biofilms and generate by-products that have highly offensive odors, are toxic, and can cause corrosion of metal surfaces by accelerating galvanic action. For example, these microorganisms reduce sulfates present in the injection water to generate hydrogen sulfide. Hydrogen sulfide has a highly offensive odor (i.e., rotten egg smell), is corrosive and reacts with metal surfaces to form insoluble iron sulfide corrosion products.

The proliferation of bacteriological contamination in lubricants and cutting fluids is a common problem due to the elevated temperatures and unsanitary conditions found in many metal working plants. It is often necessary to discard these fluids due to microbiological contamination.

In order to control the foregoing problems in various industrial processes, numerous antimicrobial agents (i.e., biocides) have been employed to eliminate, to inhibit or to reduce microbial growth. These biocides are used alone or in combination to prevent or control the problems caused by growth of microorganisms.

Biocides are classified as oxidizing or non-oxidizing, depending on their chemical composition and mode of action. Whether an oxidizing or non-oxidizing biocide is used alone or in combination is dependent upon the problematic microorganism(s), the nature of the medium to which the biocide is added, as well as specific requirements of the industry, including safety and regulatory considerations.

Oxidizing biocides have been widely used in the industry for decades, especially in pulp and paper production where strong oxidizers have been used to control microbial populations. An important aspect of using an oxidizing biocide as a microbiological control program is to apply quantities sufficient to maintain a free oxidizer residual in the process. This can be problematic in process waters that contain high concentrations of dissolved and particulate inorganic and organic materials. Such process waters exhibit a high and variable "demand" on the oxidizer (i.e., the oxidizer can react with the inorganic and organic materials and be rendered ineffective as a biocide). The type and amount of inorganic and organic materials within the process streams, therefore, will determine the demand. For example, oxidizing biocides are consumed by inorganic species such as ferrous iron, reduced manganese, sulfides, sulfites, etc. as well as organic compounds such cellulosic fibers and additives. Thus, the demand of a system will increase with increasingly higher concentrations of inorganic and organic materials along with adverse physical conditions such as temperature and pH within those systems.

In order to overcome the demand of a system and achieve a free oxidizer residual, sufficient quantities of the oxidizer must be added. Although it is technically simple to feed quantities of oxidizing biocides to exceed the demand, this is often not practical. Not only do treatment costs increase with higher addition rates, but many adverse side effects in the industrial system can be manifested. The adverse effects will be system dependent.

In paper making systems, strong oxidizers, such as sodium hypochlorite, are often used for controlling the growth of microorganisms in order to prevent adverse effects on the papermaking process. Frequently, however, strong oxidizers such as sodium hypochlorite can cause more problems on the machine than they remedy. In papermaking systems, the side effects of strong oxidizers can be, among others, increased corrosion rates, increased consumption of dyes and other costly wet end chemicals (e.g., brighteners, dry and wet strength additives, and sizing agents), and reduced felt life.

Ammonium bromide activated with sodium hypochlorite has been shown to be an effective biocide for industrial applications (U.S. Pat. No. 5,976,386). This biocide is especially effective in pulp and paper process systems. Specifically, ammonium bromide effectively reduces the total microbial community within a system (i.e., sessile as well as planktonic bacteria) and helps in the removal of slime deposits from surfaces. Moreover, it does this without interfering with other pulp and paper process and functional additives (e.g., wet and dry strength additives, size agents, dyes, etc), unlike other common oxidizer programs. Considering the benefits of an ammonium bromide-based biocide program, it is likely that the active chemical species has a mode of action that differs from hypochlorite or other strong oxidizers. Therefore, it was surprising to find a significant synergy between ammonium bromide activated with sodium hypochlorite and other biocides.

U.S. Pat. No. 6,222,071 disclosed the manufacture of high grade chloramine wherein sodium hypochlorite solution is reacted with a combined mixture of ammonia and ammonium salts at low temperatures.

SUMMARY OF THE INVENTION

The present invention is directed to synergistic mixtures (or combinations) of a nitrogenous compound activated with an oxidant and non-oxidizing biocides. In addition, the present invention is directed to the methods of controlling microbial populations in industrial process waters by administering effective amounts of the nitrogenous compound activated with an oxidant and non-oxidizing biocides to aqueous systems to result in a synergistic effect.

The present invention relates to certain combinations and processes useful for controlling the growth of microorganisms in aqueous systems and for controlling the problems resulting from uncontrolled growth of microorganisms in industrial process systems. More specifically, the present invention relates to the use of certain mixtures (or combinations) and processes or methods to prevent the growth of microorganisms in industrial process waters.

The novel mixtures (or combinations) and processes (methods) incorporating the composition of the present invention show unexpected synergistic activity against microorganisms. Specifically, the invention is directed to the mixtures or (combinations) of a nitrogenous compound activated with an oxidant and non-oxidizing biocides and the method of applying the nitrogenous compound activated with an oxidant and at least one non-oxidizing biocide to an aqueous system to result in a synergistic effect.

DETAILED DESCRIPTION OF THE INVENTION

The present invention is directed to novel synergistic biocidal mixtures (or combinations) comprising a nitrogenous compound activated by an oxidant and at least one non-oxidizing biocide in an aqueous system. These novel synergistic biocidal mixtures (or combinations) when used in combination in an aqueous system are effective in inhibiting or controlling the growth of microorganism in the aqueous system. The present invention is also directed to a method of inhibiting or controlling the growth of microorganisms by administering or adding an effective amount of a nitrogenous compound activated by an oxidant and an effective amount of at least one non-oxidizing biocide to aqueous systems, to result in a synergy index of less than 1 as defined herein.

The nitrogenous compounds activated with oxidants, when used in conjunction with non-oxidizing biocides in aqueous systems unexpectantly provided enhanced biocidal activity which is greater than that of the individual components. The microbiocidal mixtures (or combinations) of the present invention possess a high degree of slimicidal activity which could not have been predicted from the known activities of the individual ingredients comprising the combinations. The enhanced activity of the mixtures (or combinations) permit a significant reduction in the total quantity of the biocide required for an effective treatment of an aqueous system.

The nitrogenous compounds used in the present invention include, but are not limited to, ammonium salts. Additional nitrogenous compounds included methylamine, dimethylamine, ethanolamine, ethylenediamine, diethanolamine, triethanolamine, dodecylethanolamine, hexdecylethanolamine, oleic acid ethanolamine, triethylenetetramine, dibutylamine, tributylamine, glutamine, dilaurylamine, distearylamine, tallow-methylamine, coco-methylamine, n-acetylglucosamine, diphenylamine, ethanolmethylamine, diisopropanolamine, n-methylaniline, n-hexyl-n-methylamine, n-heptyl-n-methylamine, n-octyl-n-methylamine, n-nonyl-n-methylamine, n-decyl-n-methylamine, n-dodecyl-n-methylamine, n-tridecyl-n-methylamine, n-tetra-decyl-n-methylamine, n-benzyl-n-methylamine, n-phenylethyl-n-methylamine, n-phenylpropyl-n-methylamine, n-alkyl-n-ethylamines, n-alkyl-n-hydroxyethylamines, n-alkyl-n-propylamines, n-propylheptyl-n-methylamine, n-ethylhexyl-n-methylamine, n-ethylhexyl-n-butylamine, n-phenylethyl-n-methylamine, n-alkyl-n-hydroxypropylamines, n-alkyl-n-isopropylamines, n-alkyl-n-butylamines and n-alkyl-n-isobutylamines, n-alkyl-n-hydroxyalkylamines, hydrazine, urea, guanidines, biguanidines, polyamines, primary amines, secondary amines, cyclic amines, bicyclic amines, oligocyclic amines, aliphatic amines, aromatic amines, primary and secondary nitrogen containing polymers. Examples of ammonium salts include, but are not limited to, ammonium bromide, ammonium carbonate, ammonium chloride, ammonium fluoride, ammonium hydroxide, ammonium iodide, ammonium nitrate, ammonium phosphate, and ammonium sulfamate. Preferred nitrogenous compounds are ammonium bromide and ammonium chloride.

The oxidants used in the present invention include, but are not limited to, chlorine, alkali and alkaline earth hypochlorite salts, hypochlorous acid, chlorinated isocyanurates, bromine, alkali and alkaline earth hypobromite salts, hypobromous acid, bromine chloride, halogenated hydantoins, ozone and peroxy compounds such as alkali and alkaline earth perborate salts, alkali and alkaline earth percarbonate salts, alkali and alkaline earth persulfate salts, hydrogen peroxide, percarboxylic acid, and peracetic acid.

In one particular advantageous embodiment of the invention, the nitrogenous compound is ammonium bromide and the oxidant is sodium hypochlorite.

Examples of the non-oxidizing biocide useful in the invention include, but are not limited to, aldehydes, formaldehyde releasing compounds, halogenated hydrocarbons, phenolics, amides, halogenated amides, carbamates, heterocyclic compounds containing nitrogen and sulfur atoms in the ring structure, electrophilic active substances having an activated halogen group in the α-position and/or in the vinyl position to an electronegative group, nucleophilic active substance having an alkyl group and at least one leaving group, and surface active agents.

The aldehyde containing compounds can be linear, branched or aromatic. An example of aldehyde useful in the invention, but is not limited to, glutaraldehyde.

The formaldehyde releasing compounds are preferably halogenated, methylated nitro-hydrocarbons, for example 2-bromo-2-nitro-propane-1,3-diol (Bronopol).

The amides are preferably halogenated, for example 2,2-dibromo-3-nitrilopropionamide (DBNPA).

The heterocyclic compounds useful in the invention include thiazole and isothiazolinone derivatives. Some examples of heterocyclic compounds include, but are not limited to, 5-chloro-2-methyl-4-isothiazolin-3-one (CMIT) and 2-methyl-4-isothiazolin-3-one (MIT).

The surface active agents useful in the invention include detergents, wetting agents and emulsifiers. Some examples of surface active agents include, but are not limited to, long chain quaternary ammonium compounds, aliphatic diamines, guanidines and biguanidines.

Some electrophilic active substances include, but are not limited to, 1,2-dibromo-2,4-dicyanobutane, 2,2-dibromo-3-nitrilopropionamide (DBNPA), bis(trichloromethyl)sulfone, 4,5-dichloro-1,2-dithiol-3-one, 2-bromo-2-nitrostyrene, 5-chloro-2-methyl-4-isothiazolin-3-one (CMIT), 2-methyl-4-isothiazolin-3one (MIT).

The electrophilic active substance can be compounds in accordance with one or more of the following formulae:

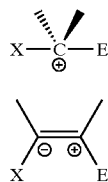

(I)

(II)

wherein

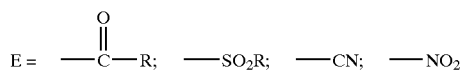

X=Halogen

The nucleophilic active substance can be compounds in accordance with one or more of the following formulae:

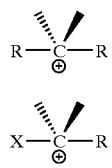

(III)

(IV)

wherein
R=SCN (Thiocyanate)
X=Halogen

Additional examples of the non-oxidizing biocide useful in the invention include, but are not limited to, 2-methyl-4-isothiazolin-3-one (MIT); 5-chloro-2-methyl-4-isothiazolin-3-one (CMIT); 2-n-octyl-4-isothiazolin-3-one; 4,5-dichloro-2-(n-octyl)-4-isothiazolin-3-one; 1,2-benziosthiazolin-3-one; glutaraldehyde; ortho-phthalaldehyde; 2,2-dibromo-3-nitrilopropionamide (DBNPA); 2-bromo-2-nitrostyrene, 2-nitrostyrene; 2-bromo-4'-hydroxyacetophenone; methylene bisthiocyanate (MBT); 2-(thiocyanomethylthio)benzothiazole; 3-iodopropynyl-N-butylcarbamate; n-alkyl dimethyl benzyl ammonium chloride; didecyl dimethyl ammonium chloride; alkenyl dimethylethyl ammonium chloride; 4,5dichloro-1,2-dithiol-3-one decylthioethylamine; 2-bromo-2-nitropropane-1,3-diol; n-dodecylguanidine hydrochloride; n-dodecylguanidine acetate; 1-(3-chloroallyl)-3,5,7-triaza-1-azoniaadamantane chloride; 1,2-dibromo-2,4-dicyanobutane; bis(1,4-bromoacetoxy)-2-butene; bis(1,2-bromoacetoxy)ethane; bis(trichloromethyl) sulfone; diiodomethyl-p-tolylsulfone; sodium orthophenylphenate; tetrahydro-3,5-dimethyl-2H-1,3,5-hydrazine-2-thine; cationic salts of dithiocarbamate derivatives; 4-chloro-3-methyl-phenol; 2,4,4'-trichloro-2'-hydroxy-diphenylether; and poly(oxyethylene(dimethyliminio)ethylene(dimethyliminio)ethylene dichloride.

The ratio of the activated nitrogenous compound to the non-oxidizing biocide is from about 10,000:1 to about 1:400 and preferably from about 5,000:1 to about 1:80.

The biocidal mixtures or methods of this invention are effective for controlling and inhibiting the growth and reproduction of microorganisms in aqueous systems and additive aqueous systems. Aqueous systems include industrial waters systems such as cooling water systems, pulp and paper systems, petroleum operations, industrial lubricants and coolants, lagoons, lakes and ponds. Aqueous systems include additive aqueous systems. In addition, the aqueous systems in which the present invention can be used includes, but is not limited to, those involved in, paints, leather, wood, wood pulp, wood chips, starch, clays, retention aids, sizing agents, defoamers, dry and wet strength additives, pigment slurries (e.g., precipitated calcium carbonate), proteinaceous materials, lumber, animal hides, vegetable tanning liquors, cosmetics, toiletry formulations, emulsions, adhesives, coatings, metalworking fluids, swimming pool water, textiles, heat exchangers, pharmaceutical formulations, geological drilling lubricants, and agrochemical compositions. An additive aqueous system is an aqueous system that is or will be added into a larger aqueous system. Such aqueous additive systems include, but are not limited to retention aids, sizing agents, defoamers, dry and wet strength additives and pigment slurries.

The dosage amounts of the non-oxidizing biocides and the nitrogenous compounds activated with oxidants required for effectiveness in this invention generally depend on the nature of the aqueous system being treated, the level of organisms present in the aqueous system, and the level of inhibition desired. A person skilled in the art could determine the amount necessary without undue experimentation.

Effective concentrations of a nitrogenous compound activated with an oxidant, on an active level basis, are from about 0.1 parts per million (ppm) to about 100 ppm by weight, (i.e., based on the weight of aqueous system being treated) preferably from about 0.5 ppm to about 50 ppm. The amount of the selected non-oxidizing biocide used in the synergistic combination will depend on the specific chemical used. In general, the amount of the non-oxidizing biocide, on an active level basis, is from about 0.01 ppm to about 40 ppm based on the weight of aqueous system being treated. Thus, with respect to the biocides, the lower and upper limits of the required concentrations substantially depend upon the specific biocide or combination of biocides used.

The nitrogenous compound activated with an oxidant can be added to the aqueous system before the non-oxidizing biocide or the non-oxidizing biocide can be added before the nitrogenous compound activated with an oxidant or they can be added simultaneously.

In one embodiment, after the controlled addition of the nitrogenous compound activated with an oxidant, the non-oxidizing biocide is then added to the aqueous system. The non-oxidizing biocide is added after the nitrogenous compound activated with an oxidant is added to the system. The time lag between the addition of nitrogenous compound and non-oxidizing biocide can be, but is not limited to, 3 hours or 2 hours or 1.5 hours or 1 hour or 30 minutes or 15 minutes.

In another embodiment, after the addition of the non-oxidizing biocide, the nitrogenous compound activated with an oxidant is added to the aqueous system. The nitrogenous compound activated with an oxidant is added after the non-oxidizing biocide is added to the system. The time lag between the addition of biocide and nitrogenous compound can be, but is not limited to, 3 hours or 2 hours or 1.5 hours or 1 hour or 30 minutes or 15 minutes.

In yet another embodiment, the nitrogenous compound, activated with an oxidant and the non-oxidizing biocide are added to the aqueous system simultaneously.

In any embodiment, the nitrogenous compound activated with an oxidant can be added pursuant to any known method that provides the desired concentration of the nitrogenous compound activated with an oxidant in the aqueous system. Similar to the nitrogenous compound activated with an oxidant addition, in any embodiment, the non-oxidizing biocide can be added pursuant to any known method that provides the desired concentration of the nitrogenous compound activated with an oxidant in the aqueous system. Either or both nitrogenous compound activated with the non-oxidizing biocides can be feed continuously, intermittently, or alternately to aqueous systems.

The biocide(s) can be added to the system as independent material(s) or in combination with other materials being added to the aqueous system being treated system. For example, the biocide(s) can be added with starch, clay, pigment slurries, precipitated calcium carbonate, retention aids, sizing aids, dry and/or wet strength additives, defoamers or other additives used in the manufacturing of pulp or paper products.

The biocides can be continuously, intermittently, or alternately added to aqueous and/or additive systems. The above feed strategies for biocide addition is dependent on the growth of the microbial population, the type of problematic microorganisms and the degree of surface fouling in a particular system. For example, ammonium bromide activated with an oxidant can be added to a system on a continuous basis while the non-oxidizing biocide is added on an intermittent basis or introduced from the treatment of additive systems (i.e., starch makedown solutions, retention aid makedown solutions, precipitated calcium carbonate slurries, etc.) or other feed points within the aqueous system (i.e., short or long loop, broke chest, saveall, thick stock, blend chest, head box).

EXAMPLES

A measured amount of ammonium bromide activated with sodium hypochlorite and a measured amount of a non-oxidizing biocide were added to a suspension of bacteria. The effectiveness of the combination of the biocides is determined by measuring growth or lack thereof after an appropriate incubation time.

A measured amount of ammonium bromide activated with sodium hypochlorite was added to a suspension of bacteria and the cell suspension incubated for a selected time after which a measured amount of a selected non-oxidizing biocide was then added to the suspension. The effectiveness of the combination of biocides was determined by measuring growth or lack thereof after an additional appropriate incubation time.

A measured amount of a selected non-oxidizing biocide was added to a suspension of bacteria and the cell suspension was incubated for a selected time after which a measured amount of ammonium bromide activated with sodium hypochlorite was then added to the suspension. The effectiveness of the combination of biocides was determined by measuring growth or lack thereof after an additional appropriate incubation time.

The efficacy of the active materials and blends was determined using a dose protocol. The actives were evaluated in synthetic white water with pH values of 5.5 and 8.0. The materials were tested against an artificial bacterial consortium containing approximately equal numbers of six bacterial strains. Although the test strains are representative of organisms present in paper mill systems, the effect is not limited to these bacteria. Two of the strains were *Klebsiella pneumonia* (ATCC 13883) and *Pseudomonas aeruginosa* (ATCC 15442). The other four strains were isolated from papermill systems and have been identified as *Curtobacterium flaccumfaciens, Burkholderia cepacia, Bacillus maroccanus*, and *Pseudomonas glathei*. Each strain was inoculated at 37° C. overnight, then suspended in sterile saline. Equal volumes of each strain were then combined to prepare the consortium. The bacterial consortium was distributed into the wells of a microtiter plate in the presence and absence of various concentrations of the active materials. The microtiter plates were incubated at 37° C. Optical density (O.D.) readings at 650 nm were taken initially ($t_0$) and after time 4 hours ($t_4$) of incubation.

The raw data was converted to "bacterial growth inhibition precentages" according to the following formula:

% Inhibition=$[(a-b) \div a]*100$ where:
a=(O.D. of control at $t_n$)–(O.D. of control at $t_0$)
b=(O.D. of treatment at $t_n$)–(O.D. of treatment at $t_0$)

The inhibition values can be plotted versus dosage for each active and the particular blend. This results in a dose response curve from which the dosage to yield 50% inhibition ($I_{50}$) can be calculated. In the examples (tables) below, the $I_{50}$ values are expressed as parts per million (ppm) of active material.

The synergism index (SI) was calculate by the equations described by F. C. Kull, P. C. Eisman, H. D. Sylwestrowicz, and R. L. Mayer (1961), *Applied Microbiology* 9, 538–541. The values are based on the amount needed to achieve a specified end point. The end point selected for these studies was 50% inhibition of bacterial growth.

Synergy Index $(SI)=(QA \div Qa)+(QB \div Qb)$ where:
QA=quantity of compound A in mixture, producing the end point
Qa=quantity of compound A, acting alone, producing the end point
QB=quantitiy of compound B in mixture, producing the end point
Qb=quantity of compound B, acting alone, producing the end point
If SI is less than 1, synergism exists; if SI is greater than 1, antagonism exists; if SI is equal to 1, an additive effect exists.

The following examples are intended to be illustrative of the present invention. However, these examples are not intended to limit the scope of the invention or its protection in any way. The examples illustrate the synergistic relationship obtained with the compositions of the present invention.

Example 1

This example shows the antagonistic activity between activated ammonium bromide (AmBr) and 2-bromo-2-nitrostyrene (BNS) under a concurrent fed strategy, against an artificial bacterial consortium in synthetic white water at pH 5.5 and 8.0.

| ppm BNS | ppm AmBr | Ratio BNS:AmBr | % Inhibition | Synergy Index |
|---|---|---|---|---|
| BNS* & AmBr @ pH 5.5 | | | | |
| 0.76 | 0.00 | 100:0 | 50 | 1.00 |
| 0.94 | 0.78 | 1.2:1.0 | 50 | 1.25 |
| 0.90 | 1.56 | 1.0:1.7 | 50 | 1.23 |
| 0.93 | 3.13 | 1.0:3.4 | 50 | 1.32 |
| 0.89 | 6.25 | 1.0:7.0 | 50 | 1.38 |
| 0.84 | 12.50 | 1.0:14.9 | 50 | 1.51 |
| 0.34 | 25.00 | 1.0:73.1 | 50 | 1.28 |
| 0.00 | 29.89 | 0:100 | 50 | 1.00 |
| BNS* & AmBr @ pH 8.0 | | | | |
| 2.48 | 0.00 | 100:0 | 50 | 1.00 |
| 3.79 | 0.78 | 4.8:1.0 | 50 | 1.55 |
| 5.06 | 1.56 | 3.2:1.0 | 50 | 2.08 |
| 3.93 | 3.13 | 1.3:1.0 | 50 | 1.66 |
| 3.10 | 6.25 | 1.0:2.0 | 50 | 1.40 |
| 4.23 | 12.50 | 1.0:3.0 | 50 | 2.01 |
| 5.64 | 25.00 | 1.0:4.4 | 50 | 2.87 |
| 0.00 | 42.14 | 0:100 | 50 | 1.00 |

*BNS—2-Bromo-2-nitrostyrene

Example 2

This example shows the synergistic activity between activated ammonium bromide (AmBr) and 2-bromo-2-nitrostyrene (BNS) under a sequential fed strategy, using a one hour delay between the additions, against an artificial bacterial consortium in synthetic white water at pH 5.5 and 8.0. Through step administration of the biocides, the negative interaction between the actives is minimized and/or eliminated to yield biocidal enhancement.

| ppm BNS | ppm AmBr | Ratio BNS:AmBr | % Inhibition | Synergy Index |
|---|---|---|---|---|
| BNS* & AmBr @ pH 5.5 | | | | |
| 0.77 | 0.00 | 100:0 | 50 | 1.00 |
| 0.57 | 0.78 | 1.0:1.4 | 50 | 0.80* |
| 0.62 | 1.56 | 1.0:2.5 | 50 | 0.92* |
| 0.58 | 3.13 | 1.0:5.4 | 50 | 0.97* |
| 0.50 | 6.25 | 1.0:12.5 | 50 | 1.08 |
| 0.17 | 12.50 | 1.0:74.4 | 50 | 1.07 |
| 0.00 | 14.67 | 0:100 | 50 | 1.00 |
| BNS* & AmBr @ pH 8.0 | | | | |
| 2.19 | 0.00 | 100:0 | 50 | 1.00 |
| 1.78 | 0.78 | 2.3:1.0 | 50 | 0.86* |
| 1.84 | 1.56 | 1.2:1.0 | 50 | 0.94* |
| 1.67 | 3.13 | 1.0:1.9 | 50 | 0.96* |
| 1.03 | 6.25 | 1.0:6.1 | 50 | 0.86* |
| 0.40 | 12.50 | 1.0:31.4 | 50 | 0.97* |
| 0.00 | 15.91 | 0:100 | 50 | 1.00 |

*BNS—2-Bromo-2-nitrostyrene

Example 3

This example shows the synergistic activity between activated ammonium bromide (AmBr) and 2-bromo-2-nitropropane-1,3-diol (Bronopol, BNPD) under a concurrent fed, against an artificial bacterial consortium in synthetic white water at pH 5.5 and 8.0.

| ppm BNPD | ppm AmBr | Ratio BNPD:AmBr | % Inhibition | Synergy Index |
|---|---|---|---|---|
| BNPD* & AmBr @ pH 5.5 | | | | |
| 1.16 | 0 | 100:0 | 50 | 1.00 |
| 1.12 | 0.78 | 1.4:1.0 | 50 | 1.01 |
| 1.14 | 1.56 | 1.0:1.4 | 50 | 1.08 |
| 1.11 | 3.13 | 1.0:2.8 | 50 | 1.15 |
| 0.87 | 6.25 | 1.0:7.2 | 50 | 1.15 |
| 0.23 | 12.50 | 1.0:55.4 | 50 | 1.01 |
| 0.00 | 15.41 | 0:100 | 50 | 1.00 |
| BNPD* & AmBr @ pH 8.0 | | | | |
| 1.34 | 0 | 100:0 | 50 | 1.00 |
| 1.08 | 0.78 | 1.4:1.0 | 50 | 0.84* |
| 1.11 | 1.56 | 1.0:1.4 | 50 | 0.91* |
| 1.03 | 3.13 | 1.0:3.0 | 50 | 0.93* |
| 0.89 | 6.25 | 1.0:7.0 | 50 | 0.98* |
| 0.46 | 12.50 | 1:27.0 | 50 | 0.99* |
| 0.00 | 19.53 | 0:100 | 50 | 1.00 |

*BNPD—2-Bromo-2-nitropropane-1,3-diol

Example 4

This example shows the synergistic activity between activated ammonium bromide (AmBr) and 1,2-dibromo-2,4-dicyanobutane (DBDCB) under a concurrent fed strategy, against an artificial bacterial consortium in synthetic white water at pH 5.5 and 8.0.

| ppm DBDCB | ppm AmBr | Ratio DBDCB:AmBr | % Inhibition | Synergy Index |
|---|---|---|---|---|
| DBDCB* & AmBr @ pH 5.5 | | | | |
| 2.70 | 0.00 | 100:0 | 50 | 1.00 |
| 2.81 | 0.78 | 3.6:1.0 | 50 | 1.07 |
| 2.86 | 1.56 | 1.8:1.0 | 50 | 1.13 |
| 2.50 | 2.38 | 1.1:1.0 | 50 | 1.03 |
| 2.19 | 3.13 | 1.0:1.4 | 50 | 0.94* |
| 2.00 | 6.25 | 1.0:3.1 | 50 | 1.01 |
| 1.33 | 12.50 | 1.0:9.4 | 50 | 1.04 |
| 1.25 | 14.37 | 1.0:11.5 | 50 | 1.09 |
| 0.63 | 19.67 | 1.0:31.5 | 50 | 1.09 |
| 0.31 | 21.82 | 1.0:69.8 | 50 | 1.07 |
| 0.16 | 19.88 | 1.0:127.2 | 50 | 0.92* |
| 0.08 | 26.04 | 1.0:333.3 | 50 | 1.16 |
| 0.04 | 22.07 | 1.0:564.9 | 50 | 0.97* |
| 0.00 | 22.99 | 0:100 | 50 | 1.00 |

-continued

| ppm DBDCB | ppm AmBr | Ratio DBDCB:AmBr | % Inhibition | Synergy Index |
|---|---|---|---|---|
| DBDCB* & AmBr @ pH 8.0 | | | | |
| 1.85 | 0.00 | 100:0 | 50 | 1.00 |
| 2.27 | 0.78 | 2.9:1.0 | 50 | 1.25 |
| 1.91 | 1.56 | 1.2:1.0 | 50 | 1.08 |
| 1.42 | 3.13 | 1.0:2.2 | 50 | 0.87* |
| 1.25 | 5.65 | 1.0:4.5 | 50 | 0.86* |
| 1.31 | 6.25 | 1.0:4.8 | 50 | 0.91* |
| 0.96 | 12.50 | 1.0:13.0 | 50 | 0.93* |
| 0.63 | 17.78 | 1.0:28.5 | 50 | 0.92* |
| 0.31 | 21.80 | 1.0:69.8 | 50 | 0.88* |
| 0.16 | 23.36 | 1.0:149.5 | 50 | 0.85* |
| 0.08 | 25.93 | 1.0:332.0 | 50 | 0.89* |
| 0.04 | 29.65 | 1.0:758.9 | 50 | 0.99* |
| 0.00 | 30.71 | 0:100 | 50 | 1.00 |

*DBDCB—1,2-Dibromo-2,4-dicyanobutane

Example 5

This example shows the synergistic activity between activated ammonium bromide (AmBr) and 2,2-dibromo-3,-nitrilopropionamide (DBNPA) under a concurrent fed strategy, against an artificial bacterial consortium in synthetic white water at pH 5.5 and 8.0.

| ppm DBNPA | ppm AmBr | Ratio DBNPA:AmBr | % Inhibition | Synergy Index |
|---|---|---|---|---|
| DBNPA & AmBr @ pH 5.5 | | | | |
| 3.08 | 0 | 100:0 | 50 | 1.00 |
| 3.50 | 0.78 | 4.5:1.0 | 50 | 1.18 |
| 3.39 | 1.56 | 2.2:1.0 | 50 | 1.18 |
| 3.29 | 3.13 | 1.1:1.0 | 50 | 1.22 |
| 3.35 | 6.25 | 1.0:1.9 | 50 | 1.39 |
| 2.72 | 12.50 | 1.0:4.6 | 50 | 1.48 |
| 2.50 | 13.79 | 1.0:5.5 | 50 | 1.47 |
| 1.25 | 19.16 | 1.0:15.3 | 50 | 1.33 |
| 0.63 | 20.32 | 1.0:32.5 | 50 | 1.18 |
| 0.31 | 19.83 | 1.0:63.5 | 50 | 1.05 |
| 0.16 | 20.56 | 1.0:131.6 | 50 | 1.04 |
| 0.08 | 20.07 | 1.0:256.9 | 50 | 0.99* |
| 0.04 | 19.56 | 1.0:500.7 | 50 | 0.95* |
| 0.02 | 19.49 | 1.0:997.9 | 50 | 0.94* |
| 0.00 | 20.86 | 0:100 | 50 | 1.00 |
| DBNPA & AmBr @ pH 8.0 | | | | |
| 2.86 | 0 | 100:0 | 50 | 1.00 |
| 2.99 | 0.78 | 3.8:1.0 | 50 | 1.08 |
| 3.23 | 1.56 | 2.1:1.0 | 50 | 1.20 |
| 3.05 | 3.13 | 1.0:1.0 | 50 | 1.21 |
| 2.94 | 6.25 | 1.0:2.1 | 50 | 1.32 |
| 2.66 | 12.50 | 1.0:4.7 | 50 | 1.50 |
| 2.50 | 14.09 | 1.0:5.6 | 50 | 1.52 |
| 1.25 | 19.22 | 1.0:15.4 | 50 | 1.32 |
| 0.63 | 20.19 | 1.0:32.3 | 50 | 1.14 |
| 0.31 | 20.24 | 1.0:64.8 | 50 | 1.03 |
| 0.16 | 20.78 | 1.0:133.0 | 50 | 1.00 |
| 0.08 | 20.70 | 1.0:265.0 | 50 | 0.97* |
| 0.04 | 20.83 | 1.0:533.4 | 50 | 0.97* |
| 0.02 | 21.24 | 1.0:1087.2 | 50 | 0.98* |
| 0.00 | 21.90 | 0:100 | 50 | 1.00 |

*DBNPA—2,2-Dibromo-3-nitrilopropionamide

Example 6

This example shows the synergistic activity between activated ammonium bromide (AmBr) and 2,2-dibromo-3,-nitrilopropionamide (DBNPA) under a sequential fed strategy, using a one hour delay between the additions, against an artificial bacterial consortium in synthetic white water at pH 5.5 and 8.0. Through stepwise administration of the biocides, the negative interaction between the actives is minimized and/or eliminated to yield an expanded range of biocidal enhancement.

| ppm DBNPA | ppm AmBr | Ratio DBNPA:AmBr | % Inhibition | Synergy Index |
|---|---|---|---|---|
| DBNPA & AmBr @ pH 5.5 | | | | |
| 3.09 | 0 | 100:0 | 50 | 1.00 |
| 2.50 | 0.24 | 10.4:1.0 | 50 | 0.82* |
| 2.04 | 0.78 | 2.6:1.0 | 50 | 0.70* |
| 1.95 | 1.56 | 1.2:1.0 | 50 | 0.72* |
| 1.69 | 3.13 | 1.0:1.9 | 50 | 0.72* |
| 1.89 | 6.25 | 1.0:3.3 | 50 | 0.96* |
| 1.79 | 12.50 | 1.0:7.0 | 50 | 1.28 |
| 1.25 | 18.32 | 1.0:14.7 | 50 | 1.43 |
| 0.63 | 20.53 | 1.0:32.8 | 50 | 1.35 |
| 0.31 | 22.85 | 1.0:73.1 | 50 | 1.38 |
| 0.16 | 19.30 | 1.0:123.5 | 50 | 1.13 |
| 0.08 | 20.32 | 1.0:260.1 | 50 | 1.17 |
| 0.04 | 19.07 | 1.0:488.2 | 50 | 1.08 |
| 0.02 | 18.86 | 1.0:965.5 | 50 | 1.06 |
| 0.00 | 17.81 | 0:100 | 50 | 1.00 |
| DBNPA & AmBr @ pH 8.0 | | | | |
| 2.33 | 0.00 | 100:0 | 50 | 1.00 |
| 1.66 | 0.78 | 2.1:1.0 | 50 | 0.75* |
| 1.59 | 1.56 | 1.0:1.0 | 50 | 0.75* |
| 1.60 | 3.13 | 1.0:2.0 | 50 | 0.83* |
| 1.77 | 6.25 | 1.0:3.5 | 50 | 1.04 |
| 2.17 | 12.50 | 1.0:5.8 | 50 | 1.49 |
| 1.25 | 20.20 | 1.0:16.2 | 50 | 1.44 |
| 0.63 | 21.43 | 1.0:34.3 | 50 | 1.23 |
| 0.31 | 22.07 | 1.0:70.6 | 50 | 1.12 |
| 0.16 | 21.31 | 1.0:136.4 | 50 | 1.02 |
| 0.08 | 21.46 | 1.0:274.7 | 50 | 0.99* |
| 0.04 | 21.86 | 1.0:559.7 | 50 | 0.99* |
| 0.02 | 22.00 | 1.0:1126.6 | 50 | 0.99* |
| 0.00 | 22.35 | 0:100 | 50 | 1.00 |

*DBNPA—2,2-Dibromo-3-nitrilopropionamide

Example 7

This example shows the synergistic activity between activated ammonium bromide (AmBr) and 4,5-dichloro-1,2-dithiol-3-one (Dithiol) under a concurrent fed strategy, against an artificial bacterial consortium in synthetic white water at pH 5.5 and 8.0.

| ppm Dithiol | ppm AmBr | Ratio Dithiol:AmBr | % Inhibition | Synergy Index |
|---|---|---|---|---|
| Dithiol* & AmBr @ pH 5.5 | | | | |
| 0.63 | 0 | 100:0 | 50 | 1.00 |
| 0.59 | 1.56 | 1.0:2.7 | 50 | 1.00 |
| 0.41 | 3.13 | 1.0:7.6 | 50 | 0.80* |
| 0.25 | 6.25 | 1.0:25.3 | 50 | 0.69* |
| 0.06 | 12.50 | 1.0:197.8 | 50 | 0.70* |
| 0 | 20.85 | 0:100 | 50 | 1.00 |
| Dithiol* & AmBr @ pH 8.0 | | | | |
| 0.84 | 0 | 100:0 | 50 | 1.00 |
| 0.51 | 1.56 | 1:3.0 | 50 | 0.69* |
| 0.29 | 3.13 | 1:10.8 | 50 | 0.50* |
| 0.15 | 6.25 | 1:42.7 | 50 | 0.48* |
| 0.04 | 12.50 | 1:318.5 | 50 | 0.65* |
| 0 | 20.59 | 0:100 | 50 | 1.00 |

*Dithiol—4,5-Dichloro-1,2-dithiol-3-one

Example 8

This example shows the synergistic activity between activated ammonium bromide (AmBr) and N-dodecylguanidine hydrochloride (DGH) under a concurrent fed strategy, against an artificial bacterial consortium in synthetic white water at pH 5.5 and 8.0.

| ppm DGH | ppm AmBr | Ratio DGH:AmBr | % Inhibition | Synergy Index |
|---|---|---|---|---|
| DGH* & AmBr @ pH 5.5 | | | | |
| 3.11 | 0.00 | 100:0 | 50 | 1.00 |
| 3.13 | 1.25 | 2.5:1.0 | 50 | 1.05 |
| 3.46 | 2.50 | 1.4:1.0 | 50 | 1.21 |
| 3.52 | 5.00 | 1.0:1.4 | 50 | 1.32 |
| 3.63 | 10.00 | 1.0:2.8 | 50 | 1.55 |
| 2.50 | 17.51 | 1.0:7.0 | 50 | 1.48 |
| 2.17 | 20.00 | 1.0:9.2 | 50 | 1.47 |
| 1.25 | 24.48 | 1.0:19.6 | 50 | 1.35 |
| 0.63 | 28.51 | 1.0:45.6 | 50 | 1.30 |
| 0.31 | 29.82 | 1.0:95.4 | 50 | 1.25 |
| 0.16 | 29.29 | 1.0:187.5 | 50 | 1.18 |
| 0.08 | 29.99 | 1.0:383.8 | 50 | 1.18 |
| 0.04 | 27.13 | 1.0:694.5 | 50 | 1.06 |
| 0.02 | 26.61 | 1.0:1362.5 | 50 | 1.03 |
| 0.01 | 25.16 | 1.0:2576.7 | 50 | 0.98* |
| 0.00 | 25.88 | 0:100 | 50 | 1.00 |
| DGH* & AmBr @ pH 8.0 | | | | |
| 1.84 | 0.00 | 100:0 | 50 | 1.00 |
| 1.82 | 1.25 | 1.5:1.0 | 50 | 1.03 |
| 1.75 | 2.50 | 1.0:1.4 | 50 | 1.04 |
| 1.76 | 5.00 | 1.0:2.8 | 50 | 1.13 |
| 1.63 | 10.00 | 1.0:6.1 | 50 | 1.23 |
| 1.25 | 22.05 | 1.0:17.6 | 50 | 1.43 |
| 1.09 | 20.00 | 1.0:18.3 | 50 | 1.28 |
| 0.63 | 26.54 | 1.0:42.5 | 50 | 1.24 |
| 0.31 | 29.99 | 1.0:96.0 | 50 | 1.19 |
| 0.16 | 31.33 | 1.0:200.5 | 50 | 1.15 |
| 0.08 | 30.18 | 1.0:386.4 | 50 | 1.07 |
| 0.04 | 29.26 | 1.0:749.0 | 50 | 1.02 |
| 0.02 | 28.04 | 1.0:1435.8 | 50 | 0.96* |
| 0.01 | 28.19 | 1.0:2887.2 | 50 | 0.96* |
| 0.00 | 29.42 | 0:100 | 50 | 1.00 |

*DGH—N-Dodecylguanidine hydrochloride

Example 9

This example shows the synergistic activity between activated ammonium bromide (AmBr) and N-Alkyl (60% C14, 30% C16, 5% C12, 5% C18) dimethyl benzyl ammonium chloride (ADBAC) under a concurrent fed strategy, against an artificial bacterial consortium in synthetic white water at pH 5.5 and 8.0.

| ppm ADBAC | ppm AmBr | Ratio ADBAC:AmBr | % Inhibition | Synergy Index |
|---|---|---|---|---|
| ADBAC* & AmBr @ pH 5.5 | | | | |
| 3.11 | 0.00 | 100:0 | 50 | 1.00 |
| 3.14 | 1.25 | 2.5:1.0 | 50 | 1.06 |
| 3.26 | 2.50 | 1.3:1.0 | 50 | 1.15 |
| 3.18 | 5.00 | 1.0:1.6 | 50 | 1.21 |
| 3.24 | 10.00 | 1.0:3.1 | 50 | 1.42 |
| 2.50 | 16.33 | 1.0:6.5 | 50 | 1.42 |
| 1.74 | 20.00 | 1.0:11.5 | 50 | 1.32 |
| 1.25 | 23.85 | 1.0:19.1 | 50 | 1.30 |
| 0.63 | 24.06 | 1.0:38.5 | 50 | 1.11 |
| 0.31 | 24.90 | 1.0:79.7 | 50 | 1.04 |
| 0.16 | 24.80 | 1.0:158.7 | 50 | 0.99* |
| 0.08 | 25.78 | 1.0:330.0 | 50 | 1.00 |
| 0.04 | 24.75 | 1.0:633.6 | 50 | 0.95* |
| 0.00 | 26.45 | 0:100 | 50 | 1.00 |
| ADBAC* & AmBr @ pH 8.0 | | | | |
| 2.42 | 0.00 | 100:0 | 50 | 1.00 |
| 2.85 | 1.25 | 2.3:1.0 | 50 | 1.22 |
| 2.71 | 2.50 | 1.1:1.0 | 50 | 1.22 |
| 2.56 | 5.00 | 1.0:2.0 | 50 | 1.25 |
| 2.50 | 7.69 | 1.0:3.1 | 50 | 1.34 |
| 2.41 | 10.00 | 1.0:4.1 | 50 | 1.39 |
| 1.36 | 20.00 | 1.0:14.7 | 50 | 1.36 |
| 1.25 | 21.03 | 1.0:16.8 | 50 | 1.35 |
| 0.63 | 22.36 | 1.0:35.8 | 50 | 1.15 |
| 0.31 | 22.81 | 1.0:73.0 | 50 | 1.04 |
| 0.16 | 24.43 | 1.0:156.3 | 50 | 1.04 |
| 0.08 | 24.80 | 1.0:317.5 | 50 | 1.02 |
| 0.04 | 24.52 | 1.0:627.8 | 50 | 0.99* |
| 0.00 | 25.12 | 0:100 | 50 | 1.00 |

*ADBAC—N-Alkyl (60% C14, 30% C16, 5% C12, 5% C18) dimethyl benzyl ammonium chloride

Example 10

This example shows the synergistic activity of activated ammonium bromide (AmBr) and didecyl dimethyl ammonium chloride (DIDAC) under a concurrent fed strategy, against an artificial bacterial consortium in synthetic white water at pH 5.5 and 8.0.

| ppm DIDAC | ppm AmBr | Ratio DIDAC:AmBr | % Inhibition | Synergy Index |
|---|---|---|---|---|
| DIDAC* & AmBr @ pH 5.5 | | | | |
| 1.82 | 0.00 | 100:0 | 50 | 1.00 |
| 1.82 | 1.25 | 1.5:1.0 | 50 | 1.05 |
| 1.65 | 2.50 | 1.0:1.5 | 50 | 1.01 |
| 1.66 | 5.00 | 1.0:3.0 | 50 | 1.12 |
| 1.75 | 10.00 | 1.0:5.7 | 50 | 1.38 |
| 1.25 | 20.09 | 1.0:16.1 | 50 | 1.53 |
| 1.01 | 20.00 | 1.0:19.7 | 50 | 1.39 |
| 0.63 | 21.43 | 1.0:34.3 | 50 | 1.24 |
| 0.31 | 23.48 | 1.0:75.1 | 50 | 1.15 |
| 0.16 | 23.41 | 1.0:149.8 | 50 | 1.07 |
| 0.08 | 21.23 | 1.0:271.8 | 50 | 0.93* |
| 0.04 | 23.74 | 1.0:607.8 | 50 | 1.01 |
| 0.00 | 23.91 | 0:100 | 50 | 1.00 |
| DIDAC* & AmBr @ pH 8.0 | | | | |
| 1.62 | 0.00 | 100:0 | 50 | 1.00 |
| 1.53 | 1.25 | 1.2:1.0 | 50 | 0.99* |
| 1.50 | 2.50 | 1.0:1.7 | 50 | 1.02 |
| 1.38 | 5.00 | 1.0:3.6 | 50 | 1.04 |
| 1.28 | 10.00 | 1.0:7.8 | 50 | 1.16 |
| 1.25 | 16.27 | 1.0:13.0 | 50 | 1.38 |
| 0.91 | 20.00 | 1.0:21.9 | 50 | 1.31 |
| 0.63 | 21.90 | 1.0:35.0 | 50 | 1.20 |
| 0.31 | 22.95 | 1.0:73.5 | 50 | 1.05 |
| 0.16 | 21.26 | 1.0:136.1 | 50 | 0.89* |
| 0.08 | 24.58 | 1.0:314.6 | 50 | 0.96* |
| 0.04 | 25.58 | 1.0:654.9 | 50 | 0.98* |
| 0.00 | 26.87 | 0:100 | 50 | 1.00 |

*DIDAC—Didecyl dimethyl ammonium chloride

Example 11

This example shows the synergistic activity between activated ammonium bromide (AmBr) and glutaraldehyde (Glut) under a concurrent fed strategy, against an artificial bacterial consortium in synthetic white water at pH 5.5 and 8.0.

| ppm Glut | ppm AmBr | Ratio Glut:AmBr | % Inhibition | Synergy Index |
|---|---|---|---|---|
| Glut* & AmBr @ pH 5.5 | | | | |
| 2.06 | 0.00 | 100:0 | 50 | 1.00 |
| 1.64 | 0.47 | 3.5:1.0 | 50 | 0.82* |
| 1.76 | 0.94 | 1.9:1.0 | 50 | 0.90* |
| 1.76 | 1.88 | 1.0:1.1 | 50 | 0.95* |
| 1.64 | 3.75 | 1.0:2.3 | 50 | 0.99* |
| 1.21 | 7.50 | 1.0:6.2 | 50 | 0.98* |
| 0.46 | 15.00 | 1.0:32.4 | 50 | 1.00 |
| 0.00 | 19.31 | 0:100 | 50 | 1.00 |
| Glut* & AmBr @ pH 8.0 | | | | |
| 6.68 | 0 | 100:0 | 50 | 1.00 |
| 5.73 | 0.47 | 12.2:1.0 | 50 | 0.88* |
| 5.64 | 0.94 | 6.0:1.0 | 50 | 0.89* |
| 5.59 | 1.88 | 3.0:1.0 | 50 | 0.92* |
| 4.98 | 3.75 | 1.3:1.0 | 50 | 0.91* |
| 3.95 | 7.50 | 1.0:1.9 | 50 | 0.93* |
| 1.05 | 15.00 | 1.0:14.3 | 50 | 0.83* |
| 0.00 | 22.31 | 0:100 | 50 | 1.00 |

*Glut—Glutaraldehyde

Example 12

This example shows the synergistic activity between activated ammonium bromide (AmBr) and 1,2-benzisothiazolin-3-one (BIT) under a concurrent fed stratey, against an artificial bacterial consortium in synthetic white water at pH 5.5 and 8.0.

| ppm BIT | ppm AmBr | Ratio BIT:AmBr | % Inhibition | Synergy Index |
|---|---|---|---|---|
| BIT* & AmBr @ pH 5.5 | | | | |
| 1.62 | 0.00 | 100:0 | 50 | 1.00 |
| 3.11 | 1.25 | 2.5:1.0 | 50 | 1.97 |
| 4.64 | 2.50 | 1.9:1.0 | 50 | 2.95 |
| 7.25 | 5.00 | 1.5:1.0 | 50 | 4.66 |
| 13.49 | 10.00 | 1.3:1.0 | 50 | 8.69 |
| 20.00 | 34.14 | 1.0:1.7 | 50 | 13.57 |
| 10.00 | 28.36 | 1.0:2.8 | 50 | 7.18 |
| 5.00 | 29.53 | 1.0:5.9 | 50 | 4.12 |
| 2.50 | 30.48 | 1.0:12.2 | 50 | 2.62 |
| 1.25 | 29.80 | 1.0:23.8 | 50 | 1.82 |
| 0.63 | 27.99 | 1.0:44.8 | 50 | 1.37 |
| 0.31 | 28.35 | 1.0:90.7 | 50 | 1.19 |
| 0.16 | 26.70 | 1.0:170.9 | 50 | 1.04 |
| 0.08 | 26.82 | 1.0:343.3 | 50 | 1.00 |
| 0.04 | 26.60 | 1.0:680.9 | 50 | 0.96* |
| 0.00 | 28.34 | 0:100 | 50 | 1.00 |
| BIT* & AmBr @ pH 8.0 | | | | |
| 3.59 | 0.00 | 100:0 | 50 | 1.00 |
| 6.12 | 1.25 | 4.9:1.0 | 50 | 1.74 |
| 7.29 | 2.50 | 2.9:1.0 | 50 | 2.10 |
| 13.09 | 5.00 | 2.6:1.0 | 50 | 3.78 |
| 17.65 | 10.00 | 1.8:1.0 | 50 | 5.19 |
| 20.00 | 53.51 | 1.0:2.7 | 50 | 7.06 |
| 10.00 | 46.91 | 1.0:4.7 | 50 | 4.09 |
| 5.00 | 40.07 | 1.0:8.0 | 50 | 2.51 |
| 2.50 | 39.69 | 1.0:15.9 | 50 | 1.80 |
| 1.25 | 37.03 | 1.0:29.6 | 50 | 1.38 |
| 0.63 | 35.86 | 1.0:57.4 | 50 | 1.17 |
| 0.31 | 36.32 | 1.0:116.2 | 50 | 1.10 |
| 0.16 | 34.26 | 1.0:219.3 | 50 | 1.00 |
| 0.08 | 33.78 | 1.0:432.4 | 50 | 0.96* |
| 0.04 | 33.49 | 1.0:857.3 | 50 | 0.94* |
| 0.00 | 35.90 | 0:100 | 50 | 1.00 |

*BIT—1,2-Benzisothiazolin-3-one

Example 13

This example shows the synergistic activity between activated ammonium bromide (AmBr) and a mixture of 5-chloro-2-methyl-4-isothiazolin-3-one and 2-methyl-4-isothiazolin-3-one (Isothiazolinone, ISO) under a concurrent fed strategy, against an artificial bacterial consortium in synthetic white water at pH 5.5 and 8.0.

| ppm Iso | ppm AmBr | Ratio Iso:AmBr | % Inhibition | Synergy Index |
|---|---|---|---|---|
| Iso* & AmBr @ pH 5.5 | | | | |
| 0.14 | 0.00 | 100:0 | 50 | 1.00 |
| 0.13 | 0.39 | 1.0:2.9 | 50 | 0.94* |
| 0.12 | 0.78 | 1.0:6.4 | 50 | 0.88* |
| 0.11 | 1.56 | 1.0:14.4 | 50 | 0.84* |
| 0.09 | 3.13 | 1.0:34.8 | 50 | 0.79* |
| 0.07 | 6.25 | 1.0:87.6 | 50 | 0.82* |
| 0.02 | 12.50 | 1.0:647.9 | 50 | 0.79* |
| 0.00 | 18.98 | 0:100 | 50 | 1.00 |
| Iso* & AmBr @ pH 8.0 | | | | |
| 0.15 | 0.00 | 100:0 | 50 | 1.00 |
| 0.15 | 0.39 | 1.0:2.5 | 50 | 1.08 |
| 0.13 | 0.78 | 1.0:5.9 | 50 | 0.95* |
| 0.12 | 1.56 | 1.0:13.5 | 50 | 0.87* |
| 0.10 | 3.13 | 1.0:31.0 | 50 | 0.83* |
| 0.08 | 6.25 | 1.0:81.6 | 50 | 0.80* |
| 0.03 | 12.50 | 1.0:394.2 | 50 | 0.76* |
| 0.00 | 23.28 | 0:100 | 50 | 1.00 |

*Iso—Isothiazolinone—a mixture of 5-chloro-2-methyl-4-isothiazolin-3-one & 2-methyl-4-isothiazolin-3-one

Example 14

This example shows the synergistic activity between activated ammonium bromide (AmBr) and 4,5-Dichloro-2-n-octyl-3(2H)-isothiazolinone under a concurrent fed strategy, against an artificial bacterial consortium in synthetic white water at pH 5.5 and 8.0.

| ppm DCOI | ppm AmBr | Ratio DCOI:AmBr | % Inhibition | Synergy Index |
|---|---|---|---|---|
| DCOI* & AmBr @ pH 5.5 | | | | |
| 0.39 | 0.00 | 100:0 | 50 | 1.00 |
| 0.43 | 1.25 | 1.0:2.9 | 50 | 1.14 |
| 0.42 | 2.50 | 1.0:5.9 | 50 | 1.17 |
| 0.34 | 5.00 | 1.0:14.8 | 50 | 1.05 |
| 0.31 | 7.73 | 1.0:24.7 | 50 | 1.08 |

-continued

| ppm DCOI | ppm AmBr | Ratio DCOI:AmBr | % Inhibition | Synergy Index |
|---|---|---|---|---|
| 0.37 | 10.00 | 1.0:27.3 | 50 | 1.30 |
| 0.25 | 20.00 | 1.0:79.2 | 50 | 1.36 |
| 0.16 | 27.76 | 1.0:177.7 | 50 | 1.39 |
| 0.08 | 30.11 | 1.0:385.4 | 50 | 1.27 |
| 0.04 | 29.64 | 1.0:758.9 | 50 | 1.15 |
| 0.02 | 28.69 | 1.0:1469.1 | 50 | 1.07 |
| 0.01 | 29.22 | 1.0:2991.7 | 50 | 1.06 |
| 0.00 | 28.13 | 0:100 | 50 | 1.00 |
| DCOI* & AmBr @ pH 8.0 | | | | |
| 1.49 | 0.00 | 100:0 | 50 | 1.00 |
| 1.43 | 1.25 | 1.1:1.0 | 50 | 1.00 |
| 1.44 | 2.50 | 1.0:1.7 | 50 | 1.04 |
| 1.36 | 5.00 | 1.0:3.7 | 50 | 1.06 |
| 1.25 | 8.61 | 1.0:6.9 | 50 | 1.09 |
| 1.17 | 10.00 | 1.0:8.5 | 50 | 1.08 |
| 0.79 | 20.00 | 1.0:25.5 | 50 | 1.11 |
| 0.63 | 26.55 | 1.0:42.5 | 50 | 1.19 |
| 0.31 | 29.28 | 1.0:93.7 | 50 | 1.06 |
| 0.16 | 32.48 | 1.0:207.8 | 50 | 1.05 |
| 0.08 | 34.33 | 1.0:439.4 | 50 | 1.05 |
| 0.04 | 34.40 | 1.0:880.7 | 50 | 1.02 |
| 0.02 | 32.89 | 1.0:1684.0 | 50 | 0.97* |
| 0.01 | 33.04 | 1.0:3383.6 | 50 | 0.96* |
| 0.00 | 34.50 | 0:100 | 50 | 1.00 |

*DCOI—4,5-Dichloro-2-n-octyl-3(2H)-isothiazolinone

Example 15

This example shows the synergistic activity between activated ammonium bromide (AmBr) and methylene bisthiocyanate (MBTC) under a concurrent fed strategy, against an artificial bacterial consortium in synthetic white water at pH 5.5 and 8.0.

| ppm MBT | ppm AmBr | Ratio MBT:AmBr | % Inhibition | Synergy Index |
|---|---|---|---|---|
| MBT* & AmBr @ pH 5.5 | | | | |
| 0.36 | 0.00 | 100:0 | 50 | 1.00 |
| 0.39 | 0.78 | 1.0:2.0 | 50 | 1.14 |
| 0.38 | 1.56 | 1.0:4.1 | 50 | 1.14 |
| 0.37 | 3.13 | 1.0:8.5 | 50 | 1.20 |
| 0.31 | 6.25 | 1.0:20.3 | 50 | 1.18 |
| 0.21 | 12.50 | 1.0:60.3 | 50 | 1.21 |
| 0.00 | 19.98 | 0:100 | 50 | 1.00 |
| MBT* & AmBr @ pH 8.0 | | | | |
| 0.71 | 0.00 | 100:0 | 50 | 1.00 |
| 0.65 | 0.78 | 1.0:1.2 | 50 | 0.95* |
| 0.63 | 1.56 | 1.0:2.5 | 50 | 0.95* |
| 0.53 | 3.13 | 1.0:5.9 | 50 | 0.87* |
| 0.47 | 6.25 | 1.0:13.2 | 50 | 0.90* |
| 0.34 | 12.50 | 1.0:36.6 | 50 | 0.93* |
| 0.00 | 27.80 | 0:100 | 50 | 1.00 |

*MBTC—Methylene bisthiocyanate

Example 16

This example shows the synergistic activity between activated ammonium bromide (AmBr) and methylene bisthiocyanate (MBTC) under a sequential fed strategy, using a one hour delay between the additions, against an artificial bacterial consortium in synthetic white water at pH 5.5 and 8.0. Through step administration of the biocides, the negative interaction between the actives is minimized and/or eliminated to yield an expanded range of biocidal enhancement.

| ppm MBT | ppm AmBr | Ratio MBT:AmBr | % Inhibition | Synergy Index |
|---|---|---|---|---|
| MBT & AmBr @ pH 5.5 | | | | |
| 0.38 | 0.00 | 100:0 | 50 | 1.00 |
| 0.46 | 0.78 | 1.0:1.7 | 50 | 1.26 |
| 0.39 | 1.56 | 1.0:4.0 | 50 | 1.15 |
| 0.36 | 3.13 | 1.0:8.7 | 50 | 1.17 |
| 0.31 | 3.73 | 1.0:11.9 | 50 | 1.09 |
| 0.25 | 6.25 | 1.0:25.4 | 50 | 1.10 |
| 0.16 | 9.43 | 1.0:60.4 | 50 | 1.09 |
| 0.08 | 11.08 | 1.0:141.8 | 50 | 1.01 |
| 0.04 | 12.50 | 1.0:307.9 | 50 | 1.01 |
| 0.04 | 12.52 | 1.0:320.5 | 50 | 1.01 |
| 0.02 | 13.08 | 1.0:669.8 | 50 | 1.00 |
| 0.01 | 13.64 | 1.0:1396.3 | 50 | 1.01 |
| 0.00 | 13.82 | 0:100 | 50 | 1.00 |
| MBTC & AmBr @ pH 8.0 | | | | |
| 0.73 | 0.00 | 100:0 | 50 | 1.00 |
| 0.85 | 0.78 | 1.1:1.0 | 50 | 1.21 |
| 0.68 | 1.56 | 1.0:2.3 | 50 | 1.03 |
| 0.63 | 1.65 | 1.0:2.6 | 50 | 0.96* |
| 0.48 | 3.13 | 1.0:6.5 | 50 | 0.86* |
| 0.33 | 6.25 | 1.0:18.7 | 50 | 0.87* |
| 0.31 | 7.04 | 1.0:22.5 | 50 | 0.89* |
| 0.16 | 10.54 | 1.0:67.5 | 50 | 0.91* |
| 0.12 | 12.50 | 1.0:101.1 | 50 | 0.91* |
| 0.08 | 13.10 | 1.0:167.6 | 50 | 0.97* |
| 0.04 | 13.23 | 1.0:338.6 | 50 | 0.92* |
| 0.02 | 14.67 | 1.0:751.3 | 50 | 0.99* |
| 0.01 | 14.59 | 1.0:1494.0 | 50 | 0.97* |
| 0.00 | 15.19 | 0:100 | 50 | 1.00 |

*MBT—Methylene bisthiocyanate

Example 17

This example shows the synergistic activity of activated ammonium bromide (AmBr) and bis(trichloromethyl)sulfone (Sulfone) under a concurrent fed strategy, against an artificial bacterial consortium in synthetic white water at pH 5.5 and 8.0.

| ppm Sulfone | ppm AmBr | Ratio Sulfone:AmBr | % Inhibition | Synergy Index |
|---|---|---|---|---|
| Sulfone* & AmBr @ pH 5.5 | | | | |
| 1.87 | 0.00 | 100:0 | 50 | 1.00 |
| 1.68 | 1.25 | 1.3:1.0 | 50 | 0.95* |
| 1.27 | 2.50 | 1.0:2.0 | 50 | 0.77* |
| 1.40 | 5.00 | 1.0:3.6 | 50 | 0.93* |
| 1.25 | 6.69 | 1.0:5.3 | 50 | 0.91* |
| 1.12 | 10.00 | 1.0:9.0 | 50 | 0.96* |
| 0.63 | 18.16 | 1.0:29.1 | 50 | 1.00* |
| 0.63 | 20.00 | 1.0:31.9 | 50 | 1.06 |
| 0.31 | 23.72 | 1.0:75.9 | 50 | 1.03 |
| 0.16 | 25.58 | 1.0:163.7 | 50 | 1.02 |
| 0.08 | 27.38 | 1.0:350.5 | 50 | 1.04 |
| 0.04 | 26.79 | 1.0:685.8 | 50 | 1.00 |
| 0.00 | 27.44 | 0:100 | 50 | 1.00 |
| Sulfone* & AmBr @ pH 8.0 | | | | |
| 8.42 | 0.00 | 100:0 | 50 | 1.00 |
| 8.38 | 1.25 | 6.7:1.0 | 50 | 1.03 |
| 8.57 | 2.50 | 3.4:1.0 | 50 | 1.09 |
| 8.18 | 5.00 | 1.6:1.0 | 50 | 1.12 |
| 7.59 | 10.00 | 1.0:1.3 | 50 | 1.20 |

-continued

| ppm Sulfone | ppm AmBr | Ratio Sulfone:AmBr | % Inhibition | Synergy Index |
|---|---|---|---|---|
| 5.00 | 16.93 | 1.0:3.4 | 50 | 1.09 |
| 3.62 | 20.00 | 1.0:5.5 | 50 | 1.02 |
| 2.50 | 23.75 | 1.0:9.5 | 50 | 1.00 |
| 1.25 | 29.92 | 1.0:23.9 | 50 | 1.03 |
| 0.63 | 32.44 | 1.0:51.9 | 50 | 1.03 |
| 0.31 | 33.68 | 1.0:107.8 | 50 | 1.03 |
| 0.16 | 32.56 | 1.0:208.4 | 50 | 0.98* |
| 0.08 | 32.32 | 1.0:413.7 | 50 | 0.97* |
| 0.04 | 32.17 | 1.0:823.6 | 50 | 0.96* |
| 0.00 | 33.80 | 0:100 | 50 | 1.00 |

*Sulfone—Bis(trichloromethyl)sulfone

Example 18

This example shows the synergistic activity between activated ammonium bromide (AmBr) and bis(trichloromethyl)sulfone (Sulfone) under a sequential fed strategy, using a one hour delay between the additions, against an artificial bacterial consortium in synthetic white water at pH 5.5 and 8.0. Through step administration of the biocides, the negative interaction between the actives is minimized and/or eliminated to yield an expanded range of biocidal enhancement.

| ppm Sulfone | ppm AmBr | Ratio Sulfone:AmBr | % Inhibition | Synergy Index |
|---|---|---|---|---|
| Sulfone* & AmBr @ pH 5.5 | | | | |
| 4.44 | 0.00 | 100:0 | 50 | 1.00 |
| 6.48 | 0.78 | 8.3:1.0 | 50 | 1.48 |
| 6.93 | 1.56 | 4.4:1.0 | 50 | 1.60 |
| 5.97 | 3.13 | 1.9:1.0 | 50 | 1.42 |
| 4.99 | 6.25 | 1.0:1.3 | 50 | 1.28 |
| 5.80 | 12.50 | 1.0:2.2 | 50 | 1.62 |
| 5.00 | 21.02 | 1.0:4.2 | 50 | 1.66 |
| 2.50 | 23.78 | 1.0:9.5 | 50 | 1.17 |
| 1.25 | 25.91 | 1.0:20.7 | 50 | 0.94* |
| 0.63 | 28.44 | 1.0:45.5 | 50 | 0.87* |
| 0.31 | 29.87 | 1.0:95.6 | 50 | 0.83* |
| 0.16 | 24.86 | 1.0:159.1 | 50 | 0.67* |
| 0.08 | 30.32 | 1.0:388.0 | 50 | 0.79* |
| 0.04 | 29.59 | 1.0:757.5 | 50 | 0.76* |
| 0.00 | 39.23 | 0:100 | 50 | 1.00 |
| Sulfone* & AmBr @ pH 8.0 | | | | |
| 10.25 | 0.00 | 100:0 | 50 | 1.00 |
| 10.04 | 0.78 | 12.8:1.0 | 50 | 1.00 |
| 11.61 | 1.56 | 7.4:1.0 | 50 | 1.18 |
| 11.64 | 3.13 | 3.7:1.0 | 50 | 1.23 |
| 7.28 | 6.25 | 1.2:1.0 | 50 | 0.90* |
| 6.11 | 12.50 | 1.0:2.0 | 50 | 0.98* |
| 5.00 | 12.92 | 1.0:2.6 | 50 | 0.89* |
| 2.50 | 17.51 | 1.0:7.0 | 50 | 0.79* |
| 1.25 | 17.81 | 1.0:14.2 | 50 | 0.68* |
| 0.63 | 18.84 | 1.0:30.1 | 50 | 0.65* |
| 0.31 | 20.29 | 1.0:64.9 | 50 | 0.66* |
| 0.16 | 17.83 | 1.0:114.1 | 50 | 0.57* |
| 0.08 | 18.46 | 1.0:236.3 | 50 | 0.58* |
| 0.00 | 32.19 | 0:100 | 50 | 1.00 |

*Sulfone—Bis(trichloromethyl)sulfone

While this invention has been described with respect to particular embodiments thereof, it is apparent that numerous other forms and modifications of the invention will be obvious to those skilled in the art. The appended claims and this invention generally should be construed to cover all such obvious forms and modifications which are within the true spirit and scope of the present invention.

What is claimed is:

1. A method for controlling the growth of microorganisms in aqueous systems comprising adding an effective amount of a nitrogenous compound activated by an oxidant and at least one non-oxidizing biocide to an aqueous system, wherein the activated nitrogenous compound comprises an activated ammonium salt selected from the group consisting of ammonium bromide, ammonium carbonate, ammonium chloride, ammonium fluoride, ammonium hydroxide, ammonium iodide, ammonium nitrate, ammonium phosphate, ammonium sulfamate and mixtures thereof, said amount of activated nitrogenous compound and non-oxidizing biocide being selected to result in a synergy index of less than 1.

2. The method of claim 1, wherein the oxidant is selected from the group consisting of chlorine, alkali and alkaline earth hypochlorite salts, hypochlorous acid, chlorinated isocyanurates, bromine, alkali and alkaline earth hypobromite salts, hypobromous acid, bromine chloride, halogenated hydantoins, ozone, a peroxy compound and combinations thereof.

3. The method of claim 2 wherein the peroxy compound is selected from the group consisting of alkali and alkaline earth perborate salts, alkali and alkaline earth percarbonate salts, alkali and alkaline earth persulfate salts, hydrogen peroxide, percarboxylic acid and peracetic acid, and combinations thereof.

4. The method of claim 1, wherein the oxidant comprises hypochlorous acid or alkali and alkaline earth hypochlorite salt.

5. The method of claim 1, wherein the non-oxidizing biocide is selected from the group consisting of aldehydes, formaldehyde releasing compounds, halogenated hydrocarbons, phenolics, amides, carbamates, heterocyclic compounds containing nitrogen and sulfur atoms in the ring structure, electrophilic active substances having an activated halogen group in the α-position and/or in the vinyl position to an electronegative group, nucleophilic active substance having an alkyl group and at least one leaving group, and surface active agents.

6. The method of claim 5, wherein the electrophilic active substance comprises a member selected from a compound in accordance with one or more of the following formulae:

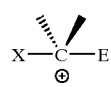

(I)

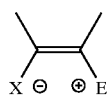

(II)

wherein

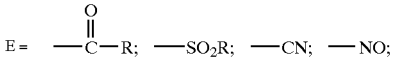

X = Halogen.

7. The method of claim 5, wherein the nucleophilic active substance comprises a member selected from a compound in accordance with one or more of the following formulae:

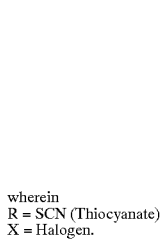

wherein
R = SCN (Thiocyanate)
X = Halogen.

8. The method of claim 1, wherein the at least one non-oxidizing biocide comprises 2,2-dibromo-3-nitrilopropionamide (DBNPA).

9. The method of claim 1, wherein the at least one non-oxidizing biocide comprises glutaraldehyde.

10. The method of claim 1, wherein the at least one non-oxidizing biocide is selected from the group consisting of thiazole derivatives, isothiazolinone derivatives and combinations thereof.

11. The method of claim 1, wherein the at least one non-oxidizing biocide is selected from the group consisting of 5-chloro-2-methyl-4-isothiazolin-3-one (CMIT) and 2-methyl-4-isothiazolin-3-one (MIT) and combinations thereof.

12. The method of claim 1, wherein the at least one non-oxidizing biocide comprises 2-bromo-2-nitro-propane-1,3-diol (Bronopol).

13. The method of claim 1, wherein the at least one non-oxidizing biocide is selected from the group consisting of long chain quaternary ammonium compound, aliphatic diamine, guanidine, biguanidine or combinations thereof.

14. The method of claim 1, wherein the at least one non-oxidizing biocide is selected from the group consisting of n-dodecylguanidine hydrochloride, n-alkyl dimethyl benzyl ammonium chloride, and didecyl dimethyl ammonium chloride, and combinations thereof.

15. The method of claim 5, wherein the electrophilic active substance is selected from the group consisting of 1,2-dibromo-2,4-dicyanobutane, 2,2-dibromo-3-nitrilopropionamide (DBNPA), bis(trichloromethyl)sulfone, 4,5-dichloro-1,2-dithiol-3-one, 2-bromo-2-nitrostyrene, 5-chloro-2-methyl-4-isothiazolin-3-one (CMIT), 2-methyl-4-isothiazolin-3-one (MIT) and combinations thereof.

16. The method of claim 1, wherein the at least one non-oxidizing biocide comprises methylene bisthiocyanate (MBT).

17. The method of claim 1, wherein the ratio of ammonium salt to the non-oxidizing biocide is from about 10,000:1 to about 1:400.

18. The method of claim 17, wherein the ratio of ammonium salt to the non-oxidizing biocide is from about 5,000:1 to about 1:80.

19. The method of claim 1, wherein the amount of ammonium salt, on an active level basis, ranges from about 0.1 to about 100 parts per million (ppm) by weight based on the weight of the aqueous system being treated and the amount of the non-oxidizing biocide, on an active level basis, ranges from about 0.01 to about 40 ppm by weight based on the weight of the aqueous system being treated.

20. The method of claim 19, wherein the amount of ammonium salt ranges from about 0.5 to about 50 ppm by weight on an active level basis and the amount of the non-oxidizing biocide ranges from about 0.01 to about 40 ppm by weight on an active level basis.

21. The method of claim 1, wherein the ammonium salt activated with an oxidant and the at least one non-oxidizing biocide are continuously, intermittently, or alternately added to the aqueous system.

22. The method of claim 1, wherein the ammonium salt and the non-oxidizing biocide are added simultaneously to the aqueous system.

23. The method of claim 1, wherein the ammonium salt is added to the aqueous system prior to the addition of the at least one non-oxidizing biocide.

24. The method of claim 1, wherein the at least one non-oxidizing biocide is added to the aqueous system prior to the addition of ammonium salt.

25. The method of claim 1, wherein the aqueous system comprises an industrial water system.

26. The method of claim 1, wherein the industrial water system is selected from the group consisting of a pulp and paper mill water system, cooling water system, and mining process waters.

27. The method of claim 1, wherein the oxidant comprises at least one of chlorine, alkali and alkaline earth hypochlorite salts, hypochlorous acid, or combinations thereof.

28. The method of claim 1, wherein the oxidant is selected from the group consisting of chlorine, alkali and alkaline earth hypochlorite salts, hypochlorous acid, alkali and alkaline earth hypobromite salts, hypobromous acid, bromine chloride, halogenated hydantoins, and combinations thereof.

29. The method of claim 1, wherein the ammonium salt is selected from the group consisting of ammonium bromide and ammonium chloride, and wherein the oxidant is selected from the group consisting of chlorine, alkali and alkaline earth hypochlorite salts, hypochlorous acid, chlorinated isocyanurates, bromine, alkali and alkaline earth hypobromite salts, hypobromous acid, bromine chloride, halogenated hydantoins, ozone, a peroxy compound and combinations thereof.

* * * * *